(12) United States Patent
Passier et al.

(10) Patent No.: US 9,115,343 B2
(45) Date of Patent: Aug. 25, 2015

(54) CARDIOMYOCYTE DIFFERENTIATION

(76) Inventors: Robert Passier, Utrecht (NL); Christine Lindsay Mummery, DJ Bilthoven (NL)

(*) Notice: Subject to any disclaimer, the term of this patent is extended or adjusted under 35 U.S.C. 154(b) by 225 days.

(21) Appl. No.: 13/430,085

(22) Filed: Mar. 26, 2012

(65) Prior Publication Data

US 2012/0178095 A1    Jul. 12, 2012

Related U.S. Application Data

(60) Division of application No. 11/628,382, filed on May 18, 2007, now Pat. No. 8,158,421, which is a continuation-in-part of application No. 10/758,554, filed on Jan. 14, 2004, which is a continuation of application No. PCT/AU02/00978, filed on Jul. 23, 2002.

(51) Int. Cl.
| | | |
|---|---|---|
| C12Q 1/68 | (2006.01) | |
| G01N 33/53 | (2006.01) | |
| G01N 33/569 | (2006.01) | |
| C12N 5/00 | (2006.01) | |
| C12N 5/02 | (2006.01) | |
| C12N 5/077 | (2010.01) | |
| C12N 5/0735 | (2010.01) | |
| G01N 33/50 | (2006.01) | |

(52) U.S. Cl.
CPC ............ *C12N 5/0657* (2013.01); *C12N 5/0606* (2013.01); *C12N 2500/25* (2013.01); *C12N 2500/99* (2013.01); *C12N 2502/02* (2013.01); *C12N 2503/02* (2013.01); *C12N 2506/02* (2013.01); *C12Q 1/68* (2013.01); *G01N 33/5008* (2013.01); *G01N 33/53* (2013.01)

(58) Field of Classification Search
CPC .............. C12N 5/0657; C12N 5/0606; C12N 2500/99; C12N 2502/02; C12N 2503/02; C12N 2506/02; C12Q 1/68; G01N 33/53; G01N 33/5008
USPC ........................... 435/6.13, 7.2, 7.3, 373, 377
See application file for complete search history.

(56) References Cited

U.S. PATENT DOCUMENTS

| 7,452,718 B2 | 11/2008 | Gold et al. |
| 2005/0054092 A1 | 3/2005 | Xu et al. |

FOREIGN PATENT DOCUMENTS

| WO | 00/70021 | 11/2000 |
| WO | 02/14469 A2 | 2/2002 |
| WO | 03/010303 A1 | 2/2003 |
| WO | 2005/090558 A1 | 9/2005 |

OTHER PUBLICATIONS

Mummery, C. et al., "Cardiomyocyte Differentiation of Mouse and Human Embryonic Stem Cells" Journal of Anatomy (2002) pp. 233-242, vol. 200(Pt 3).
Eisenberg, C.A. et al., "Mixed Cultures of Avian Blastoderm Cells and the Quail Mesoderm Cell Line QCE-6 Provide Evidence for the Pluripotentiality of Early Mesoderm" Developmental Biology (1997) pp. 167-181, vol. 191.
Passier R. et al., "Increased Cardiomyocyte Differentiation from Human Embryonic Stem Cells in Serum-Free Cultures" Stem Cells (2005) pp. 772-780, vol. 23, XP-009059684.
Sachinidis A. et al., "Identification of Plateled-Derived Growth Factor-BB as Cardiogenesis-Inducing Factor in Mouse Embryonic Stem Cells under Serum-Free Conditions" Cellular Physiology and Biochemistry (2003) pp. 423-429, vol. 13(6), XP-009075262.
Liour, S.S. et al., "Differentiation of Radial Glia from Embryonic Stem Cells in Chemically Defined Medium" Society for Neuroscience Abstract Viewer and Itinerary Planner (2003) Abstract No. 564.5, vol. 2003, XP-002456850.
Mummery, C. et al., "Differentiation of Human Embryonic Stem Cells to Cardiomyocytes: Role of Coculture with Visceral Endoderm-Like Cells" Circulation (2003) pp. 2733-2740, vol. 107(21), XP-008029536.
Xu, C. et al., "Characterization and Enrichment of Cardiomyocytes Derived from Human Embryonic Stem Cells" Circulation Research (2002) pp. 501-508, vol. 91(6), XP-002282072.
Kehat, I. et al., "Human Embryonic Stem Cells Can Differentiate into Myocytes with Structural and Functional Properties of Cardiomyocytes" The Journal of Clinical Investigation (2001) pp. 407-414, vol. 108(3), XP-002282071.
Communication pursuant to Article 94(3) EPC dated Nov. 10, 2010 in connection with European Patent Application No. 047355474.
Itskovitz-Eldor, J. et al., "Differentiation of Human Embryonic Stem Cells into Embryoid Bodies Comprising the Three Embryonic Germ Layers" Molecular Medicine (2000) pp. 88-95, vol. 6, No. 2.
Kang, Y. et al., "Proteomic Characterization of the Conditioned Media Produced by the Visceral Endoderm-Like Cell Lines HepG2 and ENF2: Toward a Defined Medium for the Osteogenic/Chondrogenic Differentiation of Embryonic Stem Cells" Stem Cells and Development (Nov. 1, 2009) pp. 77-91, vol. 18, No. 1.

*Primary Examiner* — Shin Lin Chen
(74) *Attorney, Agent, or Firm* — E. Stewart Mittler; Krista P. Kauppinen

(57) ABSTRACT

This invention provides a method for testing a factor for cardiogenicity which comprises differentiating human embryonic stem (hES) cells to cardiomyocytes in the presence and absence of the factor wherein the human embryonic stem (hES) cells are cultured under a serum free condition comprising co-culture in the presence of END-2 cells or serum-free extracellular medium therefrom, and measuring the differentiation in the presence and absence of the factor. This invention also provides a method for identifying a cardiogenic factor, which comprises differentiating human embryonic stem (hES) cells to cardiomyocytes in the presence or absence of the factor wherein the human embryonic stem (hES) cells are cultured under a serum free condition comprising co-culture in the presence of END-2 cells or serum-free extracellular medium therefrom, and identifying the factor that affects the differentiation of human embryonic stem (hES) cells to cardiomyocytes in the presence or absence of the factor.

3 Claims, 2 Drawing Sheets

CARDIOMYOCYTE DIFFERENTIATION

CROSS REFERENCE TO RELATED APPLICATIONS

Figure 1:
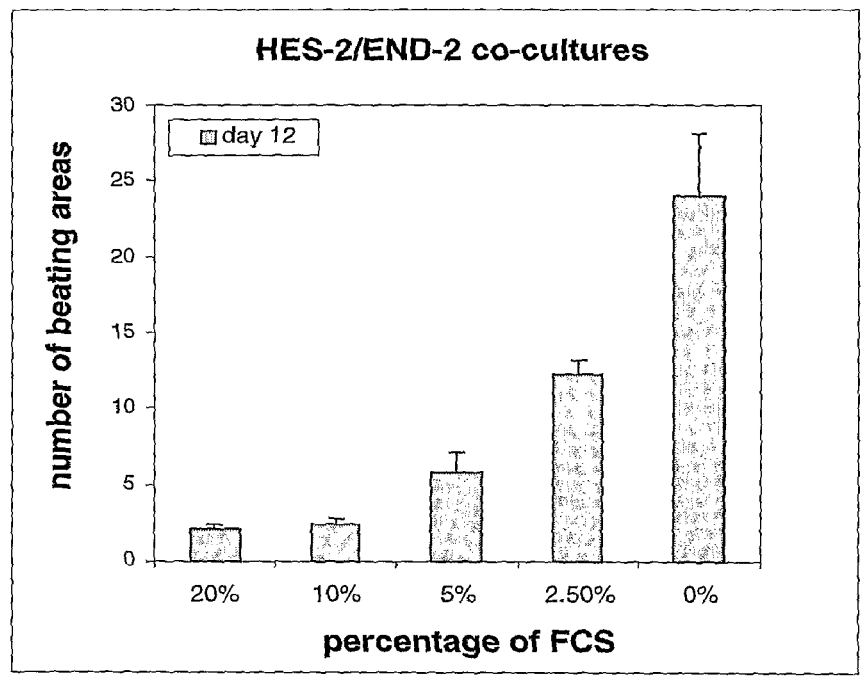

The present application is a divisional of U.S. Ser. No. 11/628,382, filed May 18, 2007, which is a continuation-in-part of U.S. Ser. No. 10/758,554, filed Jan. 14, 2004, which is a continuation of International Application No. PCT/AU2002/00978, having an international filing date of Jul. 23, 2002.

TECHNICAL FIELD

The technical field to which this invention relates is the induction of cardiomyocyte differentiation from stem cells.

BACKGROUND

Cardiomyocytes are thought to be terminally differentiated. Although a small percentage of the cells may have proliferative capacity, it is not sufficient to replace injured or dead cardiomyocytes. Death of cardiomyocytes occurs, for example, when a coronary vessel is occluded by a thrombus and the surrounding cardiomyocytes cannot be supplied with necessary energy sources from other coronary vessels. Loss of functional cardiomyocytes may lead to chronic heart failure. A potential route for restoring "normal" heart function is replacement of injured or dead cardiomyocytes by new functional cardiomyocytes. Human embryonic stem (hES) cells are a potential source of cells for cardiomyocyte replacement. Either spontaneously, or upon induction, differentiation of hES into cardiomyocytes can be achieved (1-6). Cardiomyocyte differentiation from hES cells (hES2) occurs within 12 days of co-culture with a mouse endoderm-like cell line, END-2. Based on cardiomyocyte phenotype and electrophysiology, the majority of hES-derived cardiomyocytes resemble human fetal ventricular cardiomyocytes (1, 2). However, the efficiency of cardiomyocyte differentiation from standard co-culture experiments is low.

DESCRIPTION OF THE INVENTION

In an attempt to improve efficiency of cardiomyocyte differentiation we have developed defined, serum-free conditions for testing cardiogenic factors. We demonstrate that serum-free growth itself improves the efficiency of cardiomyocyte differentiation, beating areas being detected earlier and at higher frequency than under standard serum-containing conditions.

We describe the effect of fetal calf serum (FCS) on cardiomyocyte differentiation from hES cells. A dramatic increase in the number of beating areas was observed in the absence of FCS. This increase was observed in all hES cell lines tested (hES2, hES3 and hES4). It is expected that these culture conditions for improved cardiomyocyte differentiation will be applicable at least to all HES lines from the same sources as those tested and suggested that these culture conditions for improved cardiomyocyte differentiation are applicable to all hES cell lines and hES cells in general. Furthermore, the fact that these differentiation conditions are established without fetal calf serum, and thus without the presence of animal pathogens, increases the chance that these hES-derived cardiomyocytes are suitable for cardiomyocyte transplantation in patients with heart disease.

The present invention provides a method of enhancing the efficiency of differentiation of hES cells into cardiomyocytes which method comprises incubating the cells in serum free medium. The method typically includes providing cells that induce cardiomyocyte differentiation by cell to cell contact. Differentiation to cardiomyocytes can occur via two routes, namely by spontaneous differentiation and by induced differentiation. Without wishing to be bound by theory, the present inventors hypothesise that, in the case of induced differentiation, END-2 cells, for instance, are needed for aggregation to cause local high cell densities and in inducing differentiation of nascent mesoderm. This second step could be enhanced in any human embryonic stem cell line leading to the prediction that it will work in lines other than hES. In cell lines that undergo spontaneous differentiation, it is hypothesised that local induction of embryoid bodies in endoderm occurs. Typically for induced differentiation this method will also comprise culturing the hES cell with a cell excreting at least one cardiomyocyte differentiation inducing factor or with an extracellular medium therefrom, under conditions that induce differentiation.

The present invention also provides serum free conditions for testing cardiogenic factors. The invention therefore provides a method for testing a factor for cardiogenicity which comprises testing the efficiency of differentiation of hES cells into cardiomyocytes in serum free medium in the presence and absence of the factor. Typically this method will also comprise culturing the hES cell with a cell excreting at least one cardiomyocyte differentiation inducing factor or with an extracellular medium therefrom, under conditions that induce differentiation.

The invention also provides use of serum free medium in a method of inducing differentiation of hES cells into cardiomyocytes.

Some hES cells undergo cardiogenesis spontaneously, differentiating spontaneously to somatic derivatives in embryoid bodies, reminiscent of those formed by mES cells (10).

Human embryonic stem cells co-cultured with mouse visceral endoderm (VE)-like cells form beating muscle cells, expressing cardiac specific sarcomeric proteins and ion channels. Direct comparison of electrophysiological responses demonstrates that the majority resemble human fetal ventricular cells in culture, while a minority has an atrial phenotype. This co-culture method permits induction of cardiomyocyte differentiation in hES cells that do not undergo cardiogenesis spontaneously, even at high local cell densities. Both fetal and hES-derived cardiomyocytes in culture are functionally coupled through gap junctions.

Co-culture of pluripotent hES cell lines with END-2 cells induces extensive differentiation to two distinctive cell types from different lineages. One is epithelial and forms large cystic structures staining positively for alpha-fetoprotein and is presumably extraembryonic visceral endoderm; the others are grouped in areas of high local density and beat spontaneously. These beating cells are cardiomyocytes.

The present invention provides a method for enhancing cardiomyocyte differentiation of a human embryonic stem cell (hES), the method comprising co-culturing the hES cell with a cell excreting at least one cardiomyocyte differentiation inducing factor or with an extracellular medium therefrom, under conditions that induce differentiation, in serum free medium. Typically, the cell produces a protein excretion profile that is at least substantially as produced by mouse VE-like cells.

The stem cells suitable for use in the present methods comprise both embryonic and adult stem cells and may be derived from a patient's own tissue. This would enhance compatibility of differentiated tissue grafts derived from the stem cells with the patient. In this context it should be noted that hES cells can include adult stem cells derived from a person's own tissue. Human stem cells may be genetically modified prior to use through introduction of genes that may control their state of differentiation prior to, during or after their exposure to the embryonic cell or extracellular medium from an embryonic cell. They may be genetically modified through introduction of vectors expressing a selectable marker under the control of a stem cell specific promoter such as Oct-4. The stem cells may be genetically modified at any stage with a marker so that the marker is carried through to any stage of cultivation. The marker may be used to purify the differentiated or undifferentiated stem cell populations at any stage of cultivation.

Cells providing differentiating factor(s) may be embryonic cells derived from visceral endoderm tissue or visceral endoderm like tissue isolated from an embryo. Preferably, visceral endoderm may be isolated from early postgastrulation embryos, such as mouse embryo (E7.5). Visceral endoderm or visceral endoderm like tissue can be isolated as described in (22). Characteristically the visceral endoderm may be identified by expression of alphafetoprotein and cytokeratin (ENDO-A). The embryonic cell may be an embryonal carcinoma cell, preferably one that has visceral endoderm properties. Also included are cells that express endoderm factors or are genetically manipulated to express endoderm factors.

In one embodiment, the cell producing differentiation factor(s) is a mouse VE-like cell or a cell derived therefrom. In a preferred form of this embodiment the cell is an END-2 cell.

The embryonic stem cell may be derived from a cell line or cells in culture. The embryonic cell may be derived from an embryonic cell line, preferably a cell line with characteristics of visceral endoderm, such as the END-2 cell line (23). The END-2 cell line was established by cloning from a culture of P19 EC cells treated as aggregates in suspension (embryoid bodies) with retinoic acid then replated (23). The END-2 cell line has characteristics of visceral endoderm (VE), expressing alpha-fetoprotein (AFP) and the cytoskeletal protein ENDO-A.

In another embodiment the cell is a liver parenchymal cell. In a preferred form of this embodiment the liver parenchymal cell is HepG2.

The human embryonic stem cell may be derived directly from an embryo or from a culture of embryonic stem cells [see for example (12)]. The stem cell may be derived from an embryonic cell line or embryonic tissue. The embryonic stem cells may be cells which have been cultured and maintained in an undifferentiated state.

The hES cell may be an hES cell which does not undergo cardiogenesis spontaneously or alternatively it be an hES cell that does undergo differentiation spontaneously.

The invention also provides a cardiomyocyte produced by a method of the invention.

The differentiated cardiomyocyte may express cardiac specific sarcomeric proteins and display chronotropic responses and ion channel expression and function typical of cardiomyocytes.

Preferably, the differentiated cardiomyocyte resembles a human fetal ventricular cell in culture.

In another preferred form the differentiated cardiomyocyte resembles a human fetal atrial cell in culture.

In another preferred form the differentiated cardiomyocyte resembles a human fetal pacemaker cell in culture.

It will be understood that the resemblance to these fetal cells does not necessarily extend to possessing the same level of maturity as these fetal cells and also included is a differentiated cardiomyocyte with a more mature phenotype.

The present invention provides a plurality of differentiated cardiomyocytes of the invention wherein the differentiated cardiomyocytes are coupled. The coupling may be functional or physical.

In one embodiment the coupling is through gap junctions.

In another embodiment the coupling is through adherens junctions.

In a further embodiment the coupling is electrical.

The present invention also provides a colony of differentiated cardiomyocytes produced by dissociating beating areas from differentiated cardiomyocytes of the invention.

Typically the dissociated cells are replated. Preferably they adopt a two dimensional morphology.

The present invention also provides a model for the study of human cardiomyocytes in culture, comprising differentiated cardiomyocytes of the invention. This model is useful in the development of cardiomyocyte transplantation therapies.

Further, the present invention provides an in vitro system for testing cardiovascular drugs comprising a differentiated cardiomyocyte of the invention.

The present invention also provides a mutated differentiated cardiomyocyte of the invention prepared from a mutant hES cell. It will be recognized that methods for introducing mutations into cells are well known in the art. Mutations encompassed are not only mutations resulting in the loss of a gene or protein but also those causing over expression of a gene or protein.

The present invention provides a method of studying cardiomyocyte differentiation and function (electrophysiology) comprising use of a mutated differentiated cardiomyocyte of the invention.

The present invention provides an in vitro system for testing cardiovascular drugs comprising a mutated differentiated cardiomyocyte of the invention.

The present invention provides an in vitro method for testing cardiovascular drugs comprising using a mutated differentiated cardiomyocyte of the invention as the test cell.

Ion channels play an important role in cardiomyocyte function. If we know which channels are expressed we can make hES cells lacking specific ion channels, and study the effect on cardiac differentiation and function (using electrophysiology). Furthermore, drugs specific for a cardiac ion channel can be tested on cardiomyocyte function (looking at indicators such as action potential, beating frequency, and morphological appearance).

Areas of beating hES-derived cardiomyocytes express ANF. Expression of the α-subunits of the cardiac specific L-type calcium channel (α1c) and the transient outward potassium channel (Kv4.3) are also detected, the expression of Kv4.3 preceding onset of beating by several days. RNA for the delayed rectifier potassium channel KvLQT1 is found in undifferentiated cells, but transcripts disappear during early differentiation and reappear at later stages.

Vital fluorescent staining with ryanodine or antibodies against cell surface α1c ion channels allows differentiated cardiomyocytes of the invention to be identified in mixed cultures. This may provide a means of isolating cardiomyocytes for transplantation without genetic manipulation or compromising their viability.

The present invention also provides differentiated cells produced using methods of the invention that may be used for transplantation, cell therapy or gene therapy. Preferably, the invention provides a differentiated cell produced using methods of the invention that may be used for therapeutic purposes, such as in methods of restoring cardiac function in a subject suffering from a heart disease or condition.

Another aspect of the invention is a method of treating or preventing a cardiac disease or condition. Cardiac disease is typically associated with decreased cardiac function and includes conditions such as, but not limited to, myocardial infarction, cardiac hypertrophy and cardiac arrhythmia. In this aspect of the invention, the method includes introducing an isolated differentiated cardiomyocyte cell of the invention and/or a cell capable of differentiating into a cardiomyocyte cell when treated using a method of the invention into cardiac tissue of a subject. The isolated cardiomyocyte cell is preferably transplanted into damaged cardiac tissue of a subject. More preferably, the method results in the restoration of cardiac function in a subject.

In yet another aspect of the invention there is provided a method of repairing cardiac tissue, the method including introducing an isolated cardiomyocyte cell of the invention and/or a cell capable of differentiating into a cardiomyocyte cell when treated using a method of the invention into damaged cardiac tissue of a subject.

It is preferred that the subject is suffering from a cardiac disease or condition. In the method of repairing cardiac tissue of the present invention, the isolated cardiomyocyte cell is preferably transplanted into damaged cardiac tissue of a subject. More preferably, the method results in the restoration of cardiac function in a subject.

The present invention preferably also provides a myocardial model for testing the ability of stem cells that have differentiated into cardiomyocytes to restore cardiac function.

The present invention further provides a cell composition including a differentiated cell of the present invention, and a carrier.

The term "inducing differentiation" as used herein is taken to mean causing a stem cell to develop into a specific differentiated cell type as a result of a direct or intentional influence on the stem cell. Influencing factors can include cellular parameters such as ion influx, a pH change and/or extracellular factors, such as secreted proteins, such as but not limited to growth factors and cytokines that regulate and trigger differentiation. It may include culturing the cell to confluence and may be influenced by cell density.

Preferably, the hES cell and any cell providing differentiating factor(s) are co-cultured in vitro. This typically involves introducing the stem cell to an embryonic cell monolayer produced by proliferation of the embryonic cell in culture. Preferably, the embryonic cell monolayer is grown to substantial confluence and the stem cell is allowed to grow in the presence of extracellular medium of the embryonic cells for a period of time sufficient to induce differentiation of the stem cell to a specific cell type. Alternatively, the stem cell may be allowed to grow in culture containing the extracellular medium of the embryonic cell(s), but not in the presence of the embryonic cell(s). The embryonic cells and stem cells may be separated from each other by a filter or an acellular matrix such as agar.

In general for differentiation of stem cells the stem cell can be plated on a monolayer of embryonic cells and allowed to grow in culture to induce differentiation of the stem cell.

Conditions for obtaining differentiated embryonic stem cells are typically those which are non-permissive for stem cell renewal, but do not kill stem cells or drive them to differentiate exclusively into extraembryonic lineages. A gradual withdrawal from optimal conditions for stem cell growth favours differentiation of the stem cell to specific cell types. Suitable culture conditions may include the addition of DMSO, retinoic acid, FGFs or BMPs in co-culture which could increase differentiation rate and/or efficiency.

The cell density of the embryonic cell layer typically affects its stability and performance. The embryonic cells are typically confluent. Typically, the embryonic cells are grown to confluence and are then exposed to an agent which prevents further division of the cells, such as mitomycin C. The embryonic monolayer layer is typically established 2 days prior to addition of the stem cell(s). The stem cells are typically dispersed and then introduced to a monolayer of embryonic cells. Typically, the stem cells and embryonic cells are co-cultured for a period of two to three weeks until a substantial portion of the stem cells have differentiated.

The term "extracellular medium" as used herein is taken to mean conditioned medium produced from growing an embryonic cell as herein described in a medium for a period of time so that extracellular factors, such as secreted proteins, produced by the embryonic cell are present in the conditioned medium. The medium can include components that encourage the growth of the cells, for example basal medium such as Dulbecco's minimum essential medium (DMEM), or Ham's F12 provided in serum free form where serum is a normal component of the medium. END-2 cells are cultured normally in a 1:1 mixture of DMEM with 7.5% FCS, penicillin, streptomycin and 1% non-essential amino acids. In the coculture with human stem cells the medium is replaced with human embryonic stem cell medium containing 20% or less FCS. In the case of conditioned medium from END-2 cells the conditioned medium will be prepared in serum free form as opposed to the standard 7.5% serum.

The cardiomyocytes of the invention are preferably beating. Cardiomyocytes, can be fixed and stained with $\alpha$-actinin antibodies to confirm muscle phenotype. $\alpha$-troponin, $\alpha$-tropomysin and $\alpha$-MHC antibodies also give characteristic muscle staining. Preferably, the cardiomyocytes are fixed according to methods known to those skilled in the art. More preferably, the cardiomyocytes are fixed with paraformaldehyde, preferably with about 2% to about 4% paraformaldehyde. Ion channel characteristics and action potentials of muscle cells can be determined by patch clamp, electrophysiology and RT-PCR.

Stem cells from which cardiomyocytes are to be derived can be genetically modified to bear mutations in, for example, ion channels (this causes sudden death in humans). Cardiomyocytes derived from these modified stem cells will thus be abnormal and yield a culture model for cardiac ailments associated with defective ion channels. This would be useful for basic research and for testing pharmaceuticals. Likewise, models in culture for other genetically based cardiac diseases could be created. Cardiomyocytes of the present invention can also be used for transplantation and restoration of heart function.

For instance, ischaemic heart disease is the leading cause of morbidity and mortality in the western world. Cardiac ischaemia caused by oxygen deprivation and subsequent oxygen reperfusion initiates irreversible cell damage, eventually leading to widespread cell death and loss of function. Strategies to regenerate damaged cardiac tissue by cardiomyocyte transplantation may prevent or limit post-infarction cardiac failure. The methods of enhancing stem cells to differentiate into cardiomyocytes, as hereinbefore described would be useful for treating such heart diseases. Cardiomyocytes of the invention may also be used in a myocardial infarction model for testing the ability to restore cardiac function.

The present invention preferably provides a myocardial model for testing the ability of stems cells that have differentiated into cardiomyocytes using methods of the invention to restore cardiac function. In order to test the effectiveness of cardiomyocyte transplantation in vivo, it is important to have a reproducible animal model with a measurable parameter of cardiac function. The parameters used should clearly distinguish control and experimental animals [see for example (24)] so that the effects of transplantation can be adequately determined. PV relationships are a measure of the pumping capacity of the heart and may be used as a read-out of altered cardiac function following transplantation.

A host animal, such as, but not limited to, an immunodeficient mouse may be used as a 'universal acceptor' of cardiomyocytes from various sources. The cardiomyocytes are produced by methods of the present invention.

The myocardial model of the present invention is preferably designed to assess the extent of cardiac repair following transplant of cardiomyocytes or suitable progenitors into a suitable host animal. More preferably, the host animal is an immunodeficient animal created as a model of cardiac muscle degeneration following infarct that is used as a universal acceptor of the differentiated cardiomyocytes. This animal can be any species including but not limited to murine, ovine, bovine, canine, porcine and any non-human primates. Parameters used to measure cardiac repair in these animals may include, but are not limited to, electrophysiological characteristic of heart tissue or various heart function. For instance, contractile function may be assessed in terms of volume and pressure changes in a heart. Preferably, ventricular contractile function is assessed. Methods of assessing heart function and cardiac tissue characteristics would involve techniques also known to those skilled in the field.

The present invention further provides a cell composition including a differentiated cell of the present invention, and a carrier. The carrier may be any physiologically acceptable carrier that maintains the cells. It may be PBS or other minimum essential medium known to those skilled in the field. The cell composition of the present invention can be used for biological analysis or medical purposes, such as transplantation.

The cell composition of the present invention can be used in methods of repairing or treating diseases or conditions, such as cardiac disease or where tissue damage has occurred. The treatment may include, but is not limited to, the administration of cells or cell compositions (either as partly or fully differentiated) into patients. These cells or cell compositions would result in reversal of the condition via the restoration of function as previously disclosed above through the use of animal models.

Throughout the description and claims of this specification, the word "comprise" and variations of the word, such as "comprising" and "comprises", is not intended to exclude other additives, components, integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of each claim of this application.

The present invention will now be more fully described with reference to the accompanying examples and drawings. It should be understood, however that the description following is illustrative only and should not be taken in any way as a restriction on the generality of the invention described above.

BRIEF DESCRIPTION OF THE ACCOMPANYING DRAWINGS

FIG. 1: hES-2 cells were co-cultured with mitomycin C treated END-2 cells in DMEM media containing L-glutamine, insulin-transferirin-selenium, non-essential amino acids, 90 µM β-mercaptoethanol, penicillin/streptomycin, and varying concentrations of fetal calf serum (FCS). Co-cultures were carried out in 12-well plates and beating areas were counted at 12 days after the start of co-culture. Each different condition consisted of at least 3 independent experiments. In the co-cultures containing 20% FCS the average number of beating areas in a 12-well plate was 2. With decreasing amounts of FCS in the co-culture, increasing numbers of beating areas were found. In co-cultures without serum (0% FCS) the average number of beating areas was 24.

Figure 2:
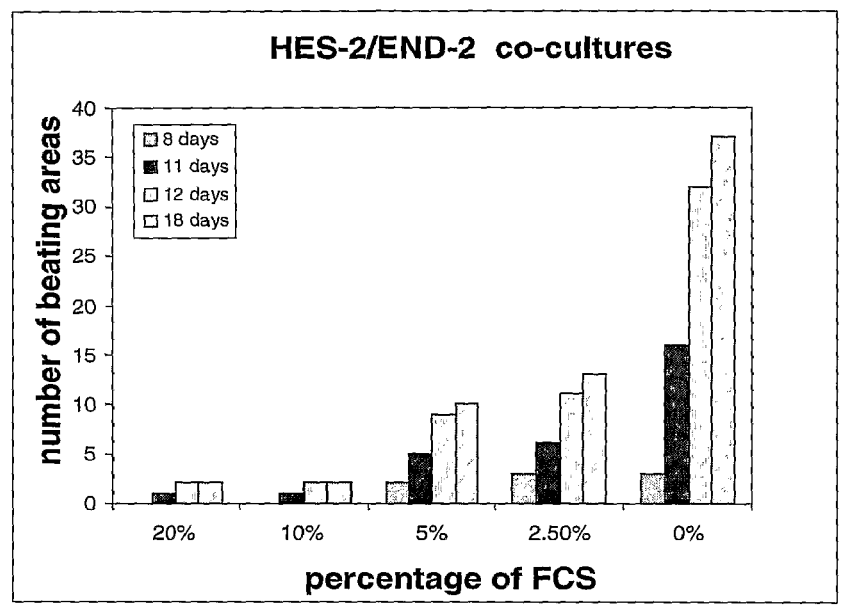

FIG. 2: hES-2 cells were co-cultured with mitomycin C treated END-2 cells in DMEM media containing L-glutamine, insulin-transferirin-selenium, non-essential amino acids, 90 µM β-mercaptoethanol, penicillin/streptomycin, and varying concentrations of fetal calf serum (FCS). Co-cultures were carried out in 12-well plates and beating areas were counted from day 8 to day 18. A linear increase in the number of beating areas was observed from day 8 to 12 under all culture conditions. Only in the complete absence of serum (0% FCS) was a slight increase in the number of beating areas observed after 18 days.

BEST METHOD AND OTHER METHODS OF CARRYING OUT THE INVENTION

When hES cells were co-cultured with visceral-endoderm (VE) like cells from the mouse, differentiation to beating muscle was initiated. Sarcomeric marker proteins, chronotropic responses and ion channel expression and function were typical of cardiomyocytes. Electrophysiology demonstrated that most cells resembled human fetal ventricular cells, with atrial-like responses in a minority population. Real-time intracellular calcium measurements, lucifer yellow injection and connexin 43 expression demonstrated that fetal and hES derived cardiomyocytes are coupled by gap junctions in culture. Antibody staining and inhibition of electrical responses by Verapamil demonstrated the presence of functional α1c calcium ion channels.

Cell Culture

END-2 cells and hES2 cells were cultured as described previously (7,11,12). To initiate cocultures, mitogenically inactive END-2 cell cultures, treated for 3 hr with mitomycin C (mit.C; 10 µg/ml) (7), replaced mouse embryonic fibroblasts (MEFs) as feeders for hES cells. Co-cultures were then grown for up to 6 weeks and scored for the presence of areas of beating muscle from 5 days onwards. HepG2 cells, a carcinoma cell line resembling liver parenchymal cells (13), were cultured in DMEM plus 10% fetal calf serum (FCS) and passaged twice weekly. Co-cultures were initiated as for END-2 cells. For electrophysiology, beating aggregates were dissociated using collagenase and replated on gelatine-coated coverslips.

Immunohistochemistry

Cells were fixed with 3.0% paraformaldehyde, then permeablized with 0.1% triton X 100. Undifferentiated hES colonies were then stained overnight at 4° C. with anti-oct4 (Sigma), visualized using the ABC complex/HPR kit (DAKO) and the Fast 3,3"-diaminobenzidine tablet set (Sigma). For immunofluorescence antibodies against α-actinin, tropomyosin and pan-cadherin (Sigma), MLC2a and 2v (gift of Dr K. Chien), α1C and Cav1.2a (Alomone labs, Israel), connexin 43 (Transduction Labs, USA) and phalloidin-Cy3 (Sigma) were used in combination with fluorescent conjugated secondary antibodies (Jackson Laboratories, U.S.A.). Confocal images (Leica Systems) were made (63× objective) from 2D projected Z-series.

Primary Human Adult and Fetal Cardiomyocytes.

Primary tissue was obtained during cardiac surgery or following abortion after individual permission using standard informed consent procedures and approval of the ethics committee of the University Medical Center, Utrecht. Adult cardiomyocytes were isolated and cultured, as reported previously (2). Fetal cardiomyocytes were isolated from fetal hearts perfused by Langendorff and cultured on glass coverslips. For (patch clamp) electrophysiology, cells were collected in Tyrode's buffer with low $Ca^{2+}$ (14).

Electrophysiology

Data were recorded from cells at 33° C. in spontaneously beating areas using an Axopatch 200B amplifier (Axon Instruments Inc., Foster City, Calif., U.S.A.). Cell attached patches were made in the whole cell voltage-clamp mode. The pipette offset, series resistance and transient cancellation were compensated; subsequent action potentials were recorded by switching to the current-clamp mode of the 200B amplifier. Output signals were digitized at 4 kHz using a Pentium III equipped with an AD/DAC LAB PC+ acquisition board (National Instruments, Austin, Tex., U.S.A.). Patch pipettes with a resistance between 1 and 3 MΩ were used. Bath medium was 140 mM NaCl, 5 mM KCL, 2 mM CaCl2, 10 mM HEPES, adjusted to pH 7.45 with NaOH. Pipette composition: 145 mM KCl, 5 mM NaCl, 2 mM CaCl2, 4 mM EGTA, 2 mM MgCl2, 10 mM HEPES, adjusted to pH 7.30 with KOH. Verapamil was used at 5 μM, as indicated.

Calcium Measurements.

Cells were labelled for 15 min at 37° C. with 10 μM fura2-AM. The light from two excitation monochromators (SPEX fluorolog SPEX Industries EDISON, N.J, U.S.A.) was rapidly alternated between 340 (8) nm and 380 (8) nm and coupled into a microscope via a UV-optic fiber. Fluorescence intensity images were recorded from living cells at a maximal rate 120 ms/pair and corrected for background fluorescence. Calibration used the minimal ratio ($R_{min}$) after addition of 5 μg/ml ionomycin and 4 mM EGTA (pH 8) to the cells and the maximal ratio ($R_{max}$), after addition of 5 μg/ml ionomycin and 10 mM $CaCl_2$. The calcium concentration was calculated as follows: $(R-R_{min})/(R_{max}-R)*sf2/sb2*K_d$ (10).

Dye Coupling

A filtered solution of 3% w/v Lucifer yellow Lithium salt (Molecular Probes, Leiden, NL) in 150 mM LiCl was microinjected through Quickfill glass microelectrodes (Clark Electromedical Instruments Pangbourne, UK). Dye was injected into one of a group of spontaneously beating cells by a 1 Hz square pulse (50% duty cycle), amplitude of $5\times10^{-9}$ A. Directly after injection confocal laser scanning microscope images were made of the injected areas.

Testing Effect of Serum

END-2 cells and hES2, hES3 and hES4 cells were cultured as previously (1,12). To initiate co-cultures, END-2 cell cultures, treated for 3 hr with mitomycin C (mit.C; 10 μg/ml), replaced mouse embryonic fibroblasts (MEFs) as feeders for hES cells. In standard co-cultures, cells are grown in DMEM media containing L-glutamine, insulin-transferrin-selenium, non-essential amino acids, 90 μM β-mercaptoethanol, penicillin/streptomycin, and 20% fetal calf serum (FCS). Co-cultures were then grown for up to 3 weeks and scored for the presence of areas of beating muscle from 5 days onwards. To study the effect on cardiomyocyte differentiation we changed the standard co-culture conditions. The percentage of FCS in the co-cultures varied from 20% FCS to 0% FCS.

The Effect of Serum on Cardiomyocyte Differentiation

To determine the effect of serum on the cardiomyocyte differentiation of hES cells in co-culture with END-2 cells, we decreased the percentage of serum to 10%, 5%, 2.5% and 0% and compared the number of beating areas in a 12-wells co-culture plate with the standard 20% FCS co-culture conditions. As shown in FIG. 1, a significant increase in the number of beating areas was observed with lower percentages of serum, with a more than 12-fold up-regulation in the complete absence of serum when compared to cultures containing 20% FCS. From day 7 onwards beating areas were observed (and occasionally as soon as day 5 or 6) in serum free conditions and a linear increase in the number of beating areas was observed until day 12. From day 12 onwards additional beating areas appeared in the absence of FCS, but at a relatively lower rate (FIG. 2).

Before hES cells can be applied clinically it is important to control their growth and differentiation. Both embryonic and adult stem cells from the mouse apparently respond to cues within the mouse embryo to differentiate to (virtually) all somatic tissues (reviewed in 15). If these cues and the signal transduction pathways they activate can be identified, this knowledge can be utilized in controlling differentiation of stem cells in culture and in vivo. We have identified (visceral-) endoderm as a cellular source of signals that result in human ES cells differentiating to cardiomyocytes with characteristics of fetal ventricular, atrial or pacemaker cells. VE (END-2) and liver parenchymal (HepG2) cells share similar protein secretion profiles so their ability to induce comparable responses in ES cells is not surprising. In contrast to mouse ES cells, in our hands human ES cells do not easily form embryoid bodies when grown as aggregates, and never show "spontaneous" differentiation to cardiomyocytes even at high cell densities in overgrowths. This contrasts with other reports (3, 4 and 9) where the hES cells do form embryoid bodies containing cardiomyocytes. Identification of a reproducible source of inductive signals nevertheless represents an important step forward. Among the cardiogenic signals emanating from endoderm that could be responsible for the effects in tissue recombination experiments in *Xenopus* and chick and in mutant zebrafish, described above, it has been suggested that BMPs, FGFs and repressors of wnt signaling may be the most important (reviewed Olson 17). Endoderm in the mouse embryo expresses BMP2 (18) and inhibitors of wnt signaling (19, 20). Direct addition of BMP2 to hES cells however, did not result in cardiomyocyte differentiation; on the contrary, they appeared to form extraembryonic endoderm (data not shown). We therefore think it unlikely that activation of the BMP signaling pathway is the primary event initiated by END-2/hES cell co-culture. Likewise, we saw no obvious effect of FGFs. These signals could however, be involved later in differentiation of nascent mesoderm to cardiomyoblasts and use of BMPs, FGFs and wnt antagonists to enhance differentiation described here is noted as possible. Late addition of the demethylating agent 5-azacytidine to developing embryoid bodies has also been shown to be more effective than early addition (9). Careful stepwise analysis of hES cell differentiation and approaches recapitulating or mimicking endogenous signals in the embryo are the most likely to increase the efficiencies of hES differentiation to specific lineages. In addition, transplantation of committed but immature cells that have retained the capacity to form functional junctions with host cells are likely to have the least chance of introducing arrythmias.

Sarcomere organization is largely determined by mechanical forces, which are relatively minor in culture compared with the intact heart. This may explain the poorly defined staining observed here which did not change over 6 weeks despite maintenance of beating (not shown). Likewise, staining for junctional proteins showed that the hES derived cardiomyocytes were very immature although real time determination of intracellular $Ca^{2+}$ concentrations clearly showed that the cells were electrically coupled.

Kehat et al (3) recently reported similar findings in independently derived hES cardiomyocytes.

In the adult mammalian myocardium, cellular $Ca^{2+}$ entry is regulated by the sympathetic nervous system. L-type $Ca^{2+}$ channel currents are markedly increased by beta-adrenergic (beta-A) agonists, which contribute to changes in rate and contractile activity of the heart.

In the developing mammalian heart, the regulation of $Ca^{2+}$ entry by this enzyme cascade has not been clearly established, because changes in receptor density and coupling to downstream elements of the signaling cascade occur as development proceeds. Our data indicate that the L-type $Ca^{2+}$ channels in hES-derived cardiomyocytes and fetal cardiomyocytes responded to adrenergic stimuli, indicating a fully developed and connected downstream pathway. Verapamil, which specifically blocks L-type $Ca^{2+}$ channels, inhibited action potentials in fetal and hES-derived cardiomyocytes as expected. This contrasts with mouse fetal myocytes and mES derived cardiomyocytes where early cells were non-responsive despite the presence of L-type $Ca^{2+}$ channels. Here, the lack of cAMP-dependent protein kinase appeared to be the limiting factor (10,16). Thus although hES-derived and early human fetal cardiomyocytes show some features of early mouse cardiomyocytes, their calcium channel modulation resembles that in the adult mouse. hES cells may thus represent an excellent system for studying changes in calcium channel function during early human development which appears to differ significantly from that in mice. Furthermore, the appropriate calcium handling makes the cells more suitable for transplantation. Interesting was the observation of cells with plateau and nonplateau type action potentials in the fetal atrial cultures. These have been described dispersed throughout the atrium of intact fetal hearts (21) and have been considered as a possible index of specialization of an atrial fibre, although their significance is not clear. The nonplateau type was not observed among the hES-derived cardiomyocytes.

Vital fluorescent staining with ryanodine or antibodies against cell surface α1c ion channels allowed these cells to be identified in mixed cultures. This may provide a means of isolating cardiomyocytes for transplantation without genetic manipulation or compromising their viability.

LITERATURE

1. Mummery, C., Ward-Van Oostwaard, D., Doevendans, P., Spijker, R., Van Den Brink, S., Hassink, R., Van Der Heyden, M., Opthof, T., Pera, M., Brutel de la Rivière, A., Passier, R. and Tertoolen, L. Differentiation of human embryonic stem cells to cardiomyocytes: role of co-culture with visceral endoderm-like cells. Circulation 107: 2733-2740, 2003.
2. Mummery C, Ward D, van den Brink C E et al. Cardiomyocyte differentiation of mouse and human embryonic stem cells. *J Anat* 2002; 200: 233-242.
3. Kehat I, Gepstein A, Spira A et al. High-resolution electrophysiological assessment of human embryonic stem cell-derived cardiomyocytes: a novel in vitro model for the study of conduction. *Circ Res* 2002; 91:659-661.
4. Kehat I, Kenyagin-Karsenti D, Snir M et al. Human embryonic stem cells can differentiate into myocytes with structural and functional properties of cardiomyocytes. *J Clin Invest* 2001; 108:407-414.
5. He J Q, Ma Y, Lee Y, Thomson J A, Kamp T J. Human embryonic stem cells develop into multiple types of cardiac myocytes: action potential characterization. *Circ Res.* 2003 11; 93(1):32-9.
6. Xu C, Police S, Rao N, Carpenter M K. Characterization and enrichment of cardiomyocytes derived from human embryonic stem cells. *Circ Res.* 2002 Sep. 20; 91(6):501-8.
7. Mummery C L, van Achterberg T A, van den Eijnden-van Raaij A J et al. Visceral endoderm-like cell lines induce differentiation of murine P19 embryonal carcinoma cells. *Differentiation.* 1991; 46:51-60.
8. Arai A, Yamamoto K, Toyama J. Murine cardiac progenitor cells require visceral embryonic endoderm and primitive streak for terminal
9. Xu C, Inokuma M S, Denham J et al. Feeder-free growth of undifferentiated human embryonic stem cells. *Nat Biotechnol* 2001; 19:971-974.
10. Doevendans P A, Kubalak S W, An R H et al. Differentiation of cardiomyocytes in floating embryoid bodies is comparable to fetal cardiomyocytes. *J Mol Cell Cardiol* 2000; 32:839-851.
11. van den Eijnden-van Raaij A J, van Achterberg T A, van der Kruijssen C M et al. Differentiation of aggregated murine P19 embryonal carcinoma cells is induced by a novel visceral endoderm-specific FGF-like factor and inhibited by activin A. *Mach Dev.* 1991; 33:157-165.
12. Reubinoff B E, Pera M F, Fong C Y et al. Embryonic stem cell lines from human blastocysts: somatic differentiation in vitro. *Nat Biotechnol* 2000; 18:399-404.
13. Knowles B B, Howe C C, Aden D P. Human hepatocellular carcinoma cell lines secrete the major plasma proteins and hepatitis B surface antigen. *Science.* 1980; 209:497-499.
14. Sipido K R, Maes M, Van de Werf F. Low efficiency of Ca2+ entry through the Na(+)—Ca2+ exchanger as trigger for Ca2+ release from the sarcoplasmic reticulum. A comparison between L-type Ca2+ current and reverse-mode Na(+)—Ca2+ exchange. *Circ Res.* 1997; 81:1034-1044.
15. Goumans M J, Zwijsen A, van Rooijen M A et al. Transforming growth factor-beta signalling in extraembryonic mesoderm is required for yolk sac vasculogenesis in mice. *Development.* 1999; 126:3473-3483.
16. An R H, Davies M P, Doevendans P A et al. Developmental changes in betaadrenergic modulation of L-type Ca2+ channels in embryonic mouse heart. *Circ Res.* 1996; 78:371-378.
17. Olson E N. Development. The path to the heart and the road not taken. *Science* 2001; 291:2327-2328.
18. Coucouvanis E, Martin G R. Signals for death and survival: a two-step mechanism for cavitation in the vertebrate embryo. *Cell.* 1995; 83:279-287.
19. Piccolo S, Agius E, Leyns L et al. The head inducer Cerberus is a multifunctional antagonist of Nodal, BMP and Wnt signals. *Nature.* 1999; 397:707-710.
20. Mukhopadhyay M, Shtrom S, Rodriguez-Esteban C et al. Dickkopf1 is required for embryonic head induction and limb morphogenesis in the mouse. *Dev Cell* 2001; 423-434.
21. Janse M K, Anderson R H, van Capelle F J et al. A combined electrophysiological and anatomical study of the human fetal heart. *Am Heart J.* 1976; 91:556-562,
22. Roelen et al, 1994 *Dev. Biol.* 166:716-728
23. Mummery et al, 1985, *Dev Biol.* 109:402-410
24. Palmen et al. (2001), Cardiovasc. Res. 50, 516-524

The claims defining the invention are as follows:

1. A method for testing a factor for cardiogenicity, said method comprising: a) differentiating human embryonic stem (hES) cells to cardiomyocytes in the presence and absence of the factor wherein the hES cells are cultured under a serum free condition comprising co-culture in the presence of mouse visceral endoderm-like (END-2) cells or serum free extracellular medium therefrom, and b) measuring the differentiation of hES cells to cardiomyocytes in the presence and absence of the factor, wherein improved efficiency of differentiation of hES cells to cardiomyocytes in the presence of the factor indicates the factor is cardiogenic.

2. A method for testing a factor for efficiency of differentiation of human embryonic stem (hES) cells to cardiomyocytes over serum containing conditions, in vitro, the method comprising: a) co-culturing the hES cells with mouse visceral endoderm-like (END-2) cells or with an extracellular medium therefrom, in the presence and absence of the factor under serum free conditions that induce differentiation and measuring the efficiency of differentiation in the presence and absence of the factor; and b) comparing the differentiation of hES cells to cardiomyocytes from a) with the differentiation of hES cells to cardiomyocytes in the presence and absence of the factor under serum containing conditions.

3. The method according to claim 2 wherein the efficiency of differentiation of hES cells to cardiomyocytes is measured from 5 days of co-culture with the mouse visceral endoderm-like (END-2) cells or with an extracellular medium therefrom.

* * * * *